United States Patent [19]

Mifune et al.

[11] 4,311,781

[45] * Jan. 19, 1982

[54] HIGHLY-SENSITIVE HIGH-CONTRAST PHOTOGRAPHIC MATERIALS

[75] Inventors: Hiroyuki Mifune; Shunji Takada; Yoshitaka Akimura; Nobuo Sakai, all of Minami-ashigara, Japan

[73] Assignee: Fuji Photo Film Co., Ltd., Kanagawa, Japan

[*] Notice: The portion of the term of this patent subsequent to Dec. 23, 1997, has been disclaimed.

[21] Appl. No.: 165,823

[22] Filed: Jul. 3, 1980

Related U.S. Application Data

[60] Continuation-in-part of Ser. No. 949,480, Oct. 10, 1978, Pat. No. 4,241,164, which is a division of Ser. No. 863,000, Dec. 21, 1977, abandoned.

[30] Foreign Application Priority Data

Dec. 30, 1976 [JP] Japan .................. 51-157910

[51] Int. Cl.$^3$ .................. G03C 1/06; G03C 5/30
[52] U.S. Cl. .................. 430/264; 430/436; 430/439; 430/440; 430/446; 430/949
[58] Field of Search .............. 430/264, 600, 613, 436, 430/439, 440, 446, 949

[56] References Cited

U.S. PATENT DOCUMENTS

| | | |
|---|---|---|
| 3,386,831 | 6/1968 | Honig et al. |
| 4,166,742 | 9/1979 | Mifune et al. |
| 4,168,977 | 9/1979 | Takada et al. |
| 4,221,857 | 9/1980 | Okutsu et al. |
| 4,237,214 | 12/1980 | Mifune et al. |
| 4,243,739 | 1/1981 | Mifune et al. |

Primary Examiner—Mary F. Downey
Attorney, Agent, or Firm—Sughrue, Mion, Zinn, Macpeak & Seas

[57] ABSTRACT

A silver halide photographic material providing very high contrast and negative image photographic characteristics comprising a support having thereon at least one silver halide photographic emulsion layer containing substantially surface latent image type mono-dispersed silver halide grains and providing a negative image, at least one hydrophilic colloid layer of the photographic material containing a compound represented by the general formula (I)

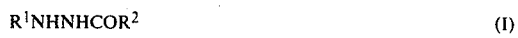

wherein
R$^1$ represents an aryl group and R$^2$ represents a hydrogen atom, a phenyl group, or an unsubstituted alkyl group having 1 to 3 carbon atoms;
and a compound represented by the general formula (II) or (III)

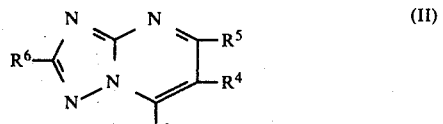

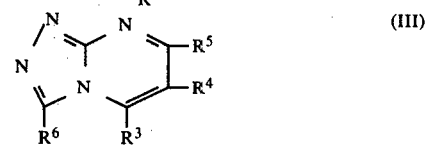

wherein R$^3$, R$^4$, R$^5$ and R$^6$, which may be the same or different, each represents a hydrogen atom, an alkyl group which may be substituted, an aryl group which may be substituted, an amino group which may be substituted, a hydroxyl group, an alkoxy group, an alkylthio group, a carbamoyl group which may be substituted, a halogen atom, a cyano group, a carboxyl group, an alkoxycarbonyl group, or a heterocyclic group; wherein R$^3$ and R$^4$ or R$^4$ and R$^5$ may combine and form a 5-membered or 6-membered ring and at least one of R$^3$ and R$^5$ represents a hydroxyl group and developing said photographic light-sensitive material with a developing solution containing a developing agent selected from the group consisting of a phenylenediamine compound and a combination of a 3-pyrazolidone compound with a hydroquinone compound.

10 Claims, No Drawings

HIGHLY-SENSITIVE HIGH-CONTRAST PHOTOGRAPHIC MATERIALS

CROSS REFERENCE OF THE RELATED APPLICATION

This application is a continuation-in-part of application Ser. No. 949,480 filed Oct. 10, 1978 now U.S. Pat. No. 4,241,164 which is a divisional of application Ser. No. 863,000 filed Dec. 21, 1977 now abandoned.

BACKGROUND OF THE INVENTION

1. Field of the Invention

This invention relates to silver halide photographic materials and, more particularly, it relates to photographic materials providing very high contrast and negative image photographic characteristics.

2. Description of the Prior Art

It is known as disclosed in, for example, U.S. Pat. No. 2,419,975 that high contrast and negative image photographic characteristics can be obtained by adding a hydrazine compound to a silver halide photographic emulsion. U.S. Pat. No. 2,419,975 discloses that very high contrast photographic characteristics of a gamma over 10 are obtained by adding a hydrazine compound to a silver chlorobromide emulsion and developing the photographic emulsion with a developer having a pH as high as 12.8. However, a strongly alkaline developer having a pH near 13 tends to be aerially oxidized and unstable, and hence cannot be stored and used for a long period of time. Also, development at such a high pH tends to cause fog.

U.S. Pat. No. 3,386,831 describes a process for stabilizing an emulsion by adding a mono-phenylhydrazide of an aliphatic carboxylic acid into an essentially surface-sensitive photographic silver halide emulsion. The object of U.S. Pat. No. 3,386,831 is to stabilize the emulsion and it differs from the objects of the present invention.

Super-high contrast photographic characteristics are very useful for the photographic reproduction of continuous tone images by dot images, which are useful for printing plate making, or the reproduction of line images in both cases of a negative image and positive image. For the purpose, a process has generally been employed in which a silver chlorobromide photographic emulsion having a silver chloride content of more than about 50 mole %, preferably more than 75 mole %, is used and the photographic emulsion layer is developed with a hydroquinone developer having a very low effective concentration of sulfite ion (usually lower than 0.1 mole/liter). However, since the sulfite ion concentration of the developer is low in the process, the developer is very unstable and cannot be stored more than 3 days. Furthermore, since a silver chlorobromide photographic emulsion having a comparatively high content of silver chloride must be used in the above-described process, it is difficult to obtain high sensitivity.

Therefore, providing super-high contrast photographic characteristics useful for the reproduction of dot images and line images using a highly-sensitive silver halide emulsion and a stable developer has been strongly desired.

It has already been found that by incorporating a compound represented by the general formula (I)

$$R^1NHNHCOR^2 \quad (I)$$

wherein $R^1$ represents an aryl group and $R^2$ represents a hydrogen atom, a phenyl group, or an unsubstituted alkyl group having 1 to 3 carbon atoms; in a negative image silver halide photographic emulsion containing substantially surface latent image type mono-dispersed silver halide grains having a mean grain size of not over 0.7 micron, super-high contrast negative photographic characteristics of a gamma as high as sometimes over 10 could be obtained using a stable developer having a comparatively high concentration of sulfite and a pH which is not very high e.g., as described in our U.S. Patent Applications Ser. Nos. 804,484, filed June 7, 1977 and Ser. No. 823,881, filed Aug. 11, 1977, (corresponding to Japanese Patent Application Nos. 66,354/76 and 96,337/76.) However, since the silver halide grains of the high contrast photographic emulsion are limited to those having a mean grain size of not over 0.7 micron, the sensitivity of the silver halide photographic emulsion obtained is not sufficiently high even due to the sensitization action by this compound represented by the general formula (I).

Japanese Patent Application (OPI) Nos. 63,914/'75; 36,130/'76 and 77,223/'76 disclose that some tetraazaindene compounds having a hydroxyl group increase the sensitivity of silver halide photographic emulsions. These compounds have been long well known as stabilizers for preventing the properties of silver halide photographic materials from changing during storage.

SUMMARY OF THE INVENTION

It has now been discovered that by further incorporating a hydroxytetraazaindene compound in the hydrophilic colloid layer of a photographic material containing a compound of the general formula (I), the sensitizing action by the compound of the general formula (I) is enhanced further than in the case of using the compound of the general formula (I) alone and, on the other hand, the sensitizing effect by the hydroxytetraazaindene compound is further enhanced.

A first object of this invention is to provide a photographic material which can provide very high contrast photographic characteristics having a gamma of over 8 even by developing the photographic material with a stable developer having a comparatively high concentration of sulfite and a comparatively low hydroxyl ion concentration.

A second object of this invention is to provide highly sensitive and very high contrasty photographic materials even though the photographic materials contain silver halide grains having a small grain size.

A further object of this invention is to provide a process of further increasing the sensitizing effect on a photographic material by a hydroxytetraazaindene compound.

It has now been found, according to this invention, that the above-described objects of this invention are attained by incorporating a compound represented by the general formula (I)

$$R^1NHNHCOR^2 \quad (I)$$

wherein $R^1$ represents a monocyclic or bicyclic aryl group and $R^2$ represents a hydrogen atom, a phenyl group, or a straight chain or branched chain alkyl group having 1 to 3 carbon atoms; and a compound represented by the general formula (II) or (III)

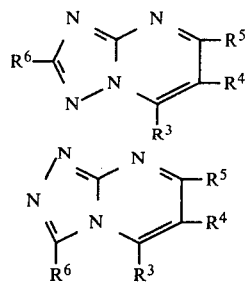

wherein $R^3$, $R^4$, $R^5$ and $R^6$, which may be the same or different, each represents a hydrogen atom, an unsubstituted or substituted straight chain, branched chain or cyclic alkyl group having 1 to 20 carbon atoms, an unsubstituted or substituted monocyclic or bicyclic aryl group, an unsubstituted or substituted amino group, a hydroxyl group, an alkoxy group having 1 to 20 carbon atoms, an alkylthio group having 1 to 6 carbon atoms, a carbamoyl group which may be substituted with an aliphatic group or an aromatic group, a halogen atom, a cyano group, a carboxyl group, an alkoxycarbonyl group having 2 to 20 carbon atoms, or a 5-membered or 6-membered heterocyclic ring containing one or more of a nitrogen atom, an oxygen atom, and a sulfur atom as a hetero-atom; $R^3$ and $R^4$ or $R^4$ and $R^5$ may combine and form a 5-membered or 6-membered ring and with at least one of $R^3$ and $R^5$ representing a hydroxyl group, in a photographic material having at least one silver halide photographic emulsion layer containing substantially surface latent image type mono-dispersed silver halide grains and developing said photographic light-sensitive material with a developing solution containing a developing agent selected from the group consisting of a phenylenediamine compound and a combination of a 3-pyrazolidone compound with a hydroquinone compound.

DETAILED DESCRIPTION OF THE INVENTION

As previously indicated, $R^1$ of general formula (I) represents a monocyclic or bicyclic aryl group. The aryl group may be substituted with one or more substituents which are not electron attractive, such as an alkyl group (which may be straight chained or branched chained) having 1 to 20 carbon atoms, an aralkyl group in which the alkyl moiety has 1 to 3 carbon atoms and may be straight chain or branched chain, an alkoxy group having 1 to 20 carbon atoms and which may be straight chain or branched chain, an amino group mono- or di-substituted with an alkyl group having 1 to 20 carbon atoms and which may be straight chain or branched chain, an aliphatic acylamino group having 2 to 21 carbon atoms which may be straight chain or branched chain, and an aromatic acylamino group which contains a monocyclic aryl moiety.

$R^2$ of general formula (I) can be a hydrogen atom, a phenyl group, or an alkyl group having 1 to 3 carbon atoms, which may be straight chained or branched chained. The alkyl group is unsubstituted. The phenyl group may be substituted and it is preferred for the substituent to be an electron attractive substituent such as, for example, a halogen atom (a chlorine atom, a bromine atom, etc.), a cyano group, a trifluoromethyl group, a carboxyl group, a sulfo group, etc.

Specific examples of substituents represented by $R^1$ in general formula (I) are a phenyl group, an α-naphthyl group, a β-naphthyl group, a p-tolyl group, a m-tolyl group, an o-tolyl group, a p-methoxyphenyl group, a m-methoxyphenyl group, a p-dimethylaminophenyl group, a p-diethylaminophenyl group, a p-(acetylamino)phenyl group, a p-(capryloylamino)phenyl group, p-(benzylamino)phenyl group, a p-benzylphenyl group, etc.

Also, specific examples of substituents represented by $R^2$ of general formula (I) other than a hydrogen atom are a methyl group, a ethyl group, an n-propyl group, a isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, a 2,5-dichlorophenyl group, etc.

A preferred substituent represented by $R^1$ of general formula (I) is a monocyclic aryl group and a particularly preferred substituent is a phenyl group and a tolyl group.

Also, preferred substituents represented by $R^2$ are a hydrogen atom, a methyl group, and a phenyl group which may be substituted. A particularly preferred substituent is a hydrogen atom.

Also, as previously indicated $R^3$, $R^4$, $R^5$ and $R^6$ of general formula (II) or (III) each representes a hydrogen atom, an unsubstituted or substituted alkyl group which may be straight chain, branched chain or cyclic, an unsubstituted or substituted monocyclic aryl group, an unsubstituted or substituted amino group, a hydroxyl group, an alkoxy group in which the alkyl moiety may be straight chain or branched chain, an alkylthio group in which the alkyl moiety may be straight chain or branched chain, an unsubstituted or substituted carbamoyl group, a halogen atom, a nitro group, a cyano group, a carboxyl group, an alkoxycarbonyl group in which the alkyl moiety may be straight chain or branched chain, or a heterocyclic group (e.g., a 5- or 6-membered ring containing one or more of nitrogen, oxygen and sulfur atoms as hetero atoms).

Examples of the above-indicated unsubstituted alkyl group are a methyl group, an ethyl group, an n-propyl group, an iso-propyl group, an n-butyl group, a t-butyl group, a hexyl group, a cyclohexyl group, a cyclopentylmethyl group, an octyl group, a dodecyl group, tridecyl group, and a heptadecyl group. The alkyl group may be substituted with one or more substituents such as, for example, a monocyclic or bicyclic aryl group, a heterocyclic ring (e.g., a 5- or 6-membered ring containing one or more of nitrogen, oxygen and sulfur atoms as hetero atoms), a halogen atom (such as a chlorine atom, a bromine atom, an iodine atom and a fluorine atom), a carboxyl group, an alkoxycarbonyl group having 2 to 6 carbon atoms in which the alkyl moiety may be straight chain or branched chain, an alkoxy group having 20 carbon atoms or less in which the alkyl moiety may be straight chain or branched chain, and a hydroxyl group. Specific examples of substituted alkyl groups are a benzyl group, a phenethyl group, a chloromethyl group, a 2-chloroethyl group, a trifluoromethyl group, a carboxymethyl group, a 2-carboxyethyl group, a 2-(methoxycarbonyl)ethyl group, an ethoxycarbonylmethyl group, a 2-methoxyethyl group, a hydroxymethyl group, a 2-hydroxyethyl group, etc.

Examples of the above-described unsubstituted aryl group are a phenyl group, a naphthyl group, etc. The aryl group may be substituted with one or more substituents such as an alkyl group having 1 to 4 carbon atoms which may be straight chain, branched chain or cyclic, a halogen atom (such as a chlorine atom, a bromine atom, an iodine atom and a fluorine atom), a carboxyl group, an alkoxycarbonyl group having 2 to 6 carbon atoms in which the alkyl moiety may be straight chain or branched chain, a hydroxyl group, an alkoxy group having 1 to 6 carbon atoms in which the alkyl moiety may be straight chain or branched chain, etc. Specific examples of substituted aryl groups are a p-tolyl group, a m-tolyl group, a p-chlorophenyl group, a p-bromophenyl group, an o-chlorophenyl group, a m-nitrophenyl group, a p-carboxyphenyl group, an o-carboxyphenyl group, an o-(methoxycarbonyl)phenyl group, a p-hydroxyphenyl group, a p-methoxyphenyl group, a m-ethoxyphenyl group, etc.

The amino group represented by $R^3$, $R^4$, $R^5$ and $R^6$ may have be substituted with a substituent such as, for example, an alkyl group, (e.g., which may be straight chain, branched chain or cyclic such as a methyl group, an ethyl group, a butyl group, etc.), an acyl group (e.g., in which the alkyl moiety may be straight chain or branched chain such as an acetyl group, a methylsulfonyl group, etc.), and the like. Specific examples of substituted amino groups are a dimethylamino group, a diethylamino group, a butylamino group, an acetylamino group, etc.

Specific examples of alkoxy groups in which the alkyl moiety may be straight chain or branched chain represented by each of $R^3$, $R^4$, $R^5$ and $R^6$ are a methoxy group, an ethoxy group, a butoxy group, and a heptadecyloxy group.

The carbamoyl group represented by $R^3$, $R^4$, $R^5$ and $R^6$ may have one or two substituents such as an alkyl group having 1 to 20 carbon atoms which may be straight chain, branched chain or cyclic and a monocyclic or bicyclic aryl group. Specific examples of substituted carbamoyl groups are a methylcarbamoyl group, a dimethylcarbamoyl group, an ethylcarbamoyl group, and a phenylcarbamoyl group.

Specific examples of alkoxycarbonyl groups in which the alkyl moiety may be straight chain or branched chain represented by each of $R^3$, $R^4$, $R^5$ and $R^6$ are a methoxycarbonyl group, an ethoxycarbonyl group, and a butoxycarbonyl group.

Specific examples of halogen atoms represented by each of $R^3$, $R^4$, $R^5$ and $R^6$ are a chlorine atom and a bromine atom.

The heterocyclic ring represented by each of $R^3$, $R^4$, $R^5$ and $R^6$ may be a single ring (e.g., a 5- or 6-membered ring containing one or more of nitrogen, oxygen and sulfur atoms as hetero atoms) or may be a condensed ring system of 2 to 3 rings (e.g., containing one or more of nitrogen, oxygen and sulfur atoms as hetero atoms) and specific examples include a furyl group, a pyridyl group, a 2-(3-methyl)benzothiazolyl group, and a 1-benzotriazolyl group.

Also, examples of the ring formed by $R^3$ and $R^4$ or by $R^4$ and $R^5$ when such combine are a cyclopentane ring, a cyclohexane ring, a cyclohexene ring, a benzene ring, a furan ring, a pyrrolidine ring, and a thiophene ring.

When $R^6$ of the general formula (II) or (III) represents a substituted alkyl group, the substituent may be a heterocyclic ring (e.g., a 5- or 6-membered ring or a condensed ring system containing one or more of nitrogen, oxygen and sulfur atoms as hetero atoms) and in this case, a substituted alkyl group represented by the following general formula (IV) is preferred;

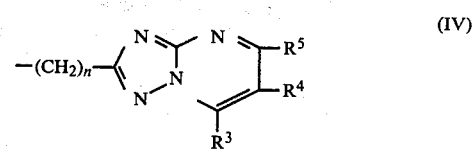

(IV)

wherein $R^3$, $R^4$ and $R^5$ each have the same meaning as in general formula (II) or (III) and n represents 2 or 4.

The silver halide grains present in the silver halide emulsion layer in this invention are substantially surface latent image type silver halide grains. In other words, they are not internal latent image type silver halide grains.

The term "substantially surface latent image type" as used in the description of this invention is defined so that when after the silver halide emulsion is exposed for 1 to 1/100 sec., and developed by surface development (A) and internal development (B) set forth below, the sensitivity obtained by surface development (A) is larger than the sensitivity obtained in internal development (B).

$$S = 100/Eh$$

wherein S is the sensitivity and Eh is the exposure amount required to obtain an intermediate density $\frac{1}{2}(D_{max}+D_{min})$ between the maximum density ($D_{max}$) and the minimum density ($D_{min}$).

Surface Development (A)

A photographic material is developed for 10 minutes at a temperature of 20° C. in a developer having the following composition;

| N-methyl-p-aminophenol (hemisulfate) | 2.5 g |
| Ascorbic acid | 10 g |
| Sodium Metaborate (tetrahydrate) | 35 g |
| Potassium Bromide | 1 g |
| Water to make | 1 liter |

Internal Development (B)

A photographic material is processed for 10 minutes at about 20° C. in a bleach solution containing 3 g/liter of a hexacyanoferrate and 0.0125 g/liter of phenosafranine, then washed with water for 10 minutes, and developed for 10 minutes at 20° C. in a developer having the following composition;

| N-methyl-p-aminophenol (hemisulfate) | 2.5 g |
| Ascorbic acid | 10 g |
| Sodium Metaborate (tetrahydrate) | 35 g |
| Potassium Bromide | 1 g |
| Sodium Thiosulfate | 3 g |
| Water to make | 1 liter |

If the silver halide emulsion used in this invention is not substantially of the surface latent image type, the photographic material thus processed results in a positive image in addition to a negative image.

The mean grain size of the surface latent image type silver halide grains present in the silver halide photographic emulsion layer or layers used in this invention containing not over 250 g of binder per mole of silver halide may be larger than 0.7 micron but is preferably not over 0.7 micron. It is necessary for 90% by weight or number based on the total silver halide grains to have a grain size in a range of ±40% of the average grain size (generally, such an emulsion is called a monodispersed emulsion). The term "mean grain size" is well known to persons skilled in the art of silver halide photography and can be easily understood by those skilled in the art. The grain size means the diameter of the grains when the silver halide grains are spherical or substantially spherical. When the grains are cubic, the grain size is defined by the length of the side edge multiplied by $\sqrt{4/\pi}$. The mean grain size is determined by an algebraic mean value or a geometric mean value based on the projected area of the grains. The method of determining the mean grain size is described in detail in, for example, C. E. K. Mees and T. H. James; *The Theory of the Photographic Process;* 3rd Ed., pages 36–43, MacMillan Co. (1966).

The photographic materials of this invention have the feature that the photographic materials exhibit high sensitivity even if the mean grain size of silver halide used for the photographic materials is small.

The silver halide in the silver halide photographic emulsions used in this invention may be silver chloride, silver bromide, silver chlorobromide, silver iodobromide, or silver iodochlorobromide. In using silver iodobromide or silver iodochloro-bromide, it is preferred for the silver iodide content to be 10 mole % or less. According to this invention, silver chlorobromide (or silver iodochlorobromide) with a large silver bromide content, silver iodobromide or silver bromide can be used, and hence a higher sensitivity than in the case of using a conventional lithographic type super-high contrast photographic material can be easily obtained. Where silver chloride is employed, it is preferred for the silver chloride content to be 80 mole % or less, preferably 50 mole % or less, of the total silver halides.

The photographic material of this invention has at least one substantially surface latent image type photographic silver halide emulsion layer and it is preferred for the amount of binder present in this emulsion layer to be not over 250 g per mole of the silver halide present in the emulsion layer. That is, when the silver halide photographic emulsion layer contains a binder in an amount not over 250 g per mole of silver halide, very high contrast photographic characteristics can be easily obtained.

Gelatin is advantageously used as the binder or the protective colloid of the silver halide photographic emulsions used in this invention, but other hydrophilic colloids can be also used. For example, gelatin derivatives, graft polymers of gelatin and other polymers, albumin, casein, and other proteins; cellulose derivatives such as hydroxyethyl cellulose, carboxymethyl cellulose, cellulose sulfate esters, etc.; saccharide derivatives such as sodium alginate, starch derivatives, etc.; and various synthetic hydrophilic polymers such as polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc., can be used.

Lime-treated gelatin as well as acid-treated gelatin may be used as the gelatin and further hydrolyzed products of gelatin and enzyme decomposition products of gelatin may be also used.

Examples of gelatin derivatives which can be used in this invention are the products obtained by reaction of gelatin and various compounds such as acid halides, acid anhydrides, isocyanates, bromoacetic acid, alkanesultones, vinylsulfoneamides, maleinimide compounds, polyalkyleneoxides, epoxy compounds, etc. Other specific examples of suitable gelatin derivatives are also described in, for example, U.S. Pat. Nos. 2,614,928; 3,132,945; 3,186,846; and 3,312,553; British Pat. Nos. 861,414; 1,033,189; and 1,005,784; and Japanese Patent Publication No. 26,845/'67.

Examples of the above-described gelatin graft polymers which can be used in this invention include graft polymers prepared by grafting homopolymers or copolymers of vinylic monomers such as acrylic acid, methacrylic acid, derivatives of these acids (e.g., the esters and amides), acrylonitrile, styrene, etc., to gelatin. In particular, graft polymers of gelatin and polymers which are compatible with gelatin to some extent, for example, polymers of acrylic acid, methacrylic acid, acrylamide, methacrylamide, hydroxyalkyl methacrylate, etc., are preferred. Examples of these graft polymers are specifically described in, for example, U.S. Pat. Nos. 2,763,625; 2,831,767; and 2,956,884.

Typical examples of synthetic hydrophilic polymers which can be used in this invention are described in, for example, German Patent Application (OLS) No. 2,312,708; U.S. Pat. Nos. 3,620,751 and 3,879,205 and Japanese Patent Publication No. 7561/'68.

The silver halide emulsions used in this invention may be chemically unsensitized but preferably have been sensitized. Known chemical sensitization methods for silver halide emulsions which can be used include a sulfur sensitization method, a reductive sensitization method, and a noble metal sensitization method. A typical noble metal sensitization method is a gold sensitization method and gold complex salts are mainly used as the typical gold compounds for the gold sensitization. Complex salts of other noble metals than gold, such as the complex salts of platinum, palladium, iridium, etc., may be used.

The reductive sensitization method may be employed to an extent that fog formation does not hinder practical use.

A preferred chemical sensitization method for the practice of this invention is a sulfur sensitization.

Suitable sulfur sensitizers which can be used include sulfur compounds present in gelatin as well as other various sulfur compounds such as thiosulfates, thioureas, thiazoles, rhodanines, etc. Specific examples of sulfur compounds are described in, for example, U.S. Pat. Nos. 1,574,944; 2,278,947; 2,410,689; 2,728,668; 3,501,313; and 3,656,955.

Preferred compounds of the compounds represented by general formula (I) are those represented by general formula (Ia)

R$^1$NHNHCHO　　　　　　　　　　　　(Ia)

wherein R$^1$ has the same meaning as in general formula (I).

Particularly preferred compounds of the compounds represented by general formula (Ia) are those represented by general formula (Ib)

R$^{11}$NHNHCHO　　　　　　　　　　　　(Ib)

wherein R$^{11}$ represents an unsubstituted phenyl group or a tolyl group.

Specific examples of compounds represented by general formula (I) are illustrated below although the compounds which can be used in this invention are not to be construed as being limited to these examples.

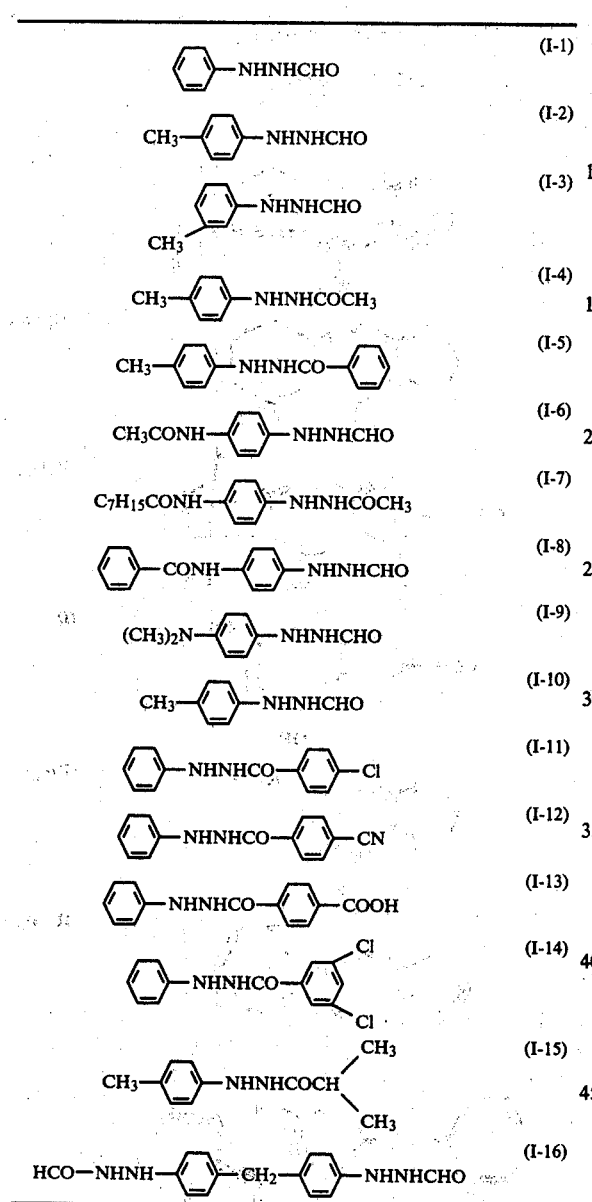

The compounds represented by the general formula (I) can be synthesized by reacting hydrazines with formic acid or by reacting hydrazines with acyl halides. Starting material hydrazines such as

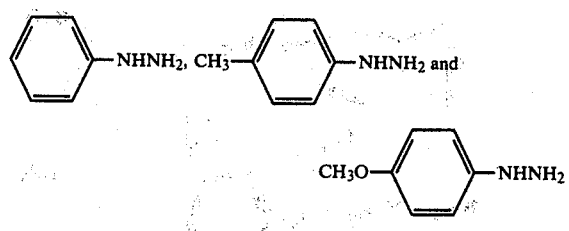

are commercially available and hydrazines of the formula

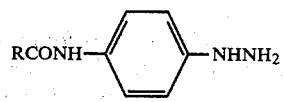

where R represents an alkyl group can be synthesized by reduction of a p-nitrophenylhydrazine. Suitable acyl halides which can be used include aliphatic acyl halides such as acetyl chloride, propionyl chloride, butyryl chloride, etc., and aromatic acyl halides such as benzoyl chloride, toluoyl chloride, etc. The reaction can be conducted in a solvent such as benzene, chloroform, pyridine, triethylamine, etc., and at a temperature of about 0° C. to about 100° C., preferably 0° C. to 70° C. A suitable molar ratio of the hydrazine to the acyl halide in the presence of a base such as pyridine or triethylamine which acts as a hydrogen halide acceptor for the hydrogen halide formed as a by-product ranges from about 1:1 to about 1:3, preferably 1:1.2 to 1:1.5 and in the absence of such a base ranges from about 1:0.3 to about 1:1, preferably 1:0.45 to 1:0.5. Hydrogen halide accepting agents such as triethylamine and pyridine can be employed in an amount of about one mole or more per mol of the acyl halide used.

Examples of synthesis of the compounds represented by the general formula (I) are described below. Unless otherwise indicated herein, all parts, percents, ratios and the like are by weight.

Specific examples of the preparation of these compounds are shown below.

SYNTHESIS EXAMPLE 1

Preparation of Compound (I-2)

While stirring 110 g of formic acid at 25°-30° C., 107 g of p-tolylhydrazine was added thereto gradually. Thereafter, the mixture was stirred for 20 minutes at 50° C. After ice-cooling the reaction mixture to about 10° C., the crystals formed were recovered by filtration and recrystallized from 550 ml of acetonitrile to provide 54.4 g of colorless acicular crystals having a melting point of 176°-177° C.

SYNTHESIS EXAMPLE 2

Preparation of Compound (I-5)

While stirring 100 ml of acetonitrile at 25°-30° C., 15 g of p-tolylhydrazine was added to the acetonitrile. Then, 15 g of benzoyl chloride was gradually added dropwise to the mixture at 25°-30° C. and thereafter, the mixture was stirred for 6 hours at 25°-30° C. After ice-cooling to about 10° C., the crystals obtained were recovered by filtration and recrystallized from benzene to provide 7 g of colorless acicular crystals having a melting point of 146° C.

Where the compound of general formula (I) employed in this invention is incorporated into the photographic material, the compound may be incorporated in the surface latent image type silver halide photographic emulsions or may be incorporated into other emulsion layers or non-light sensitive layers (for example, a protective layer, interlayers, an antihalation layer, etc.).

The amount of the compound of general formula (I) in the photographic material of this invention is usually about $10^{-4}$ to about $10^{-1}$ mole/mole-Ag of the silver halide grains present per unit area. A preferred amount of the compound of general formula (I) is $10^{-3}$ to $5\times10^{-2}$ mole/mole-Ag, in particular, $5\times10^{-3}$ to $5\times10^{-2}$ mole/mole-Ag.

Where the compound of general formula (I) is incorporated in a photographic emulsion, ordinary methods wherein additives are added to the photographic emulsion can be used. For example, when the compound of general formula (I) is insoluble or sparingly soluble in water, the compound is dissolved in an appropriate organic solvent which is miscible with water such as alcohols, ethers, glycols, ketones, esters, amides, etc., which must not, however, adversely influence the photographic characteristics of the photographic emulsion, and then the compound is added to the photographic emulsion as an organic solvent solution thereof. Furthermore, the compound may be incorporated in the photographic emulsion using methods well known in the art of adding water-insoluble (or so-called oil soluble) couplers to photographic emulsions in the form of a dispersion. When the compound is added to a coating composition for a non-sensitive layer, the same methods as described above can be employed.

Specific examples of compounds represented by general formulae (II) and (III) are illustrated below. The present invention is not to be construed as being limited to these specific examples.

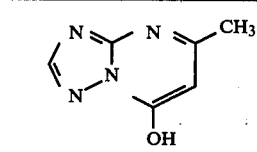  (II-1)

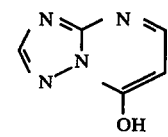  (II-2)

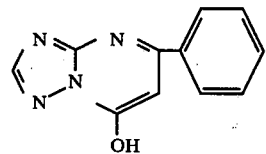  (II-3)

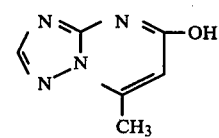  (II-4)

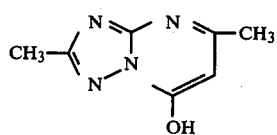  (II-5)

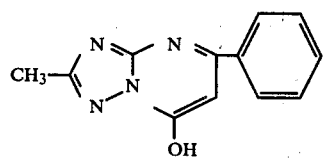  (II-6)

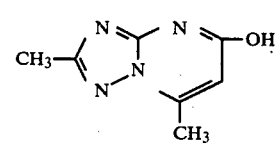  (II-7)

-continued

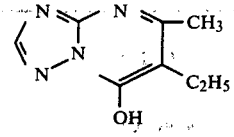  (II-8)

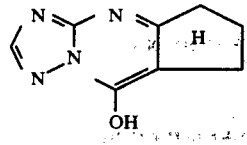  (II-9)

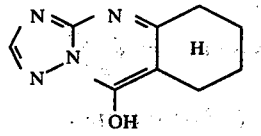  (II-10)

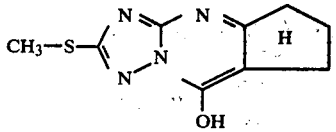  (II-11)

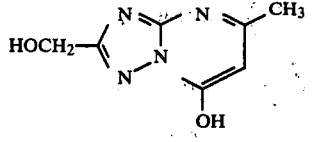  (II-12)

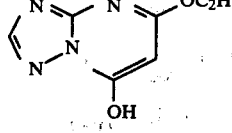  (II-13)

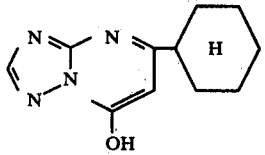  (II-14)

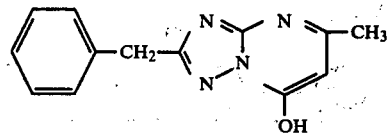  (II-15)

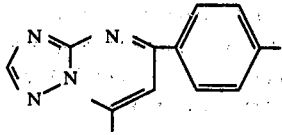  (II-16)

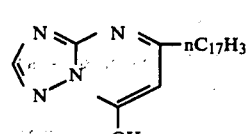  (II-17)

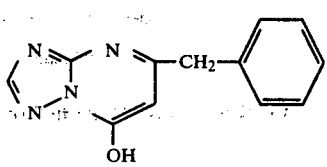  (II-18)

The compounds of general formula (II) can be easily prepared by reference to the descriptions appearing in Bulow and Haas; *Berichte;* Vol. 42, 4638(1907) and ibid. Vol. 43, 375(1910); Allen et al; *Journal of Organic Chemistry,* Vol. 24, 796(1959); De Cat and Dormel: *Bull. Soc. Chim. Belg.;* Vol. 60, 69(1951); and Cook et al; *Rec. Trav. Chem.;* Vol. 69, 34(1950).

Also, the compounds of general formula (III) can be easily prepared by reference to the descriptions appearing in Bower and Doyle; *Journal of the Chemical Society;* 727(1957) and Allen et al; *Journal of Organic Chemistry;* Vol. 24, 787(1959).

Where the compound represented by general formula (II) or (III) is incorporated in the photographic material of this invention, the compound may be present in a silver halide photographic emulsion or may be incorporated in layers other than the silver halide photographic emulsion layer, such as a protective layer, interlayers, a filter layer, an antihalation layer, etc. It is, however, preferred for the compound of general formula (II) or (III) to be incorporated in the surface latent image type silver halide photographic emulsion layer together with a compound of general formula (I).

The amount of the compound represented by general formula (II) or (II) is about $10^{-5}$ to about $3\times10^{-1}$ mole, in particular $3\times10^{-4}$ to $10^{-1}$ mole, per mole of silver to the silver halide contained in the same area of a silver halide photographic emulsion layer as that of the compound but it is preferred to select the optimum content of the compound depending on the grain size of the silver halide emulsion, the composition of the silver halide, the method and degree of the chemical sensitization employed, the relation thereof with the photographic emulsion layer containing the compound, and the kind of the compound. The method of testing for sensitization is well known to one skilled in the art and can be easily routinely accomplished.

To incorporate the compound of the general formula (II) or (III) in a silver halide emulsion layer or another non-light sensitive hydrophilic colloid layer, the compound may be added to the silver halide emulsion or the coating composition for the non-light sensitive layer and the same method as the case of incorporating the compound of the general formula (I) into a photographic emulsion described above can be used. More particularly, the compound may be added to an aqueous solution of a hydrophilic colloid as a solution of an organic solvent miscible with water, such as alcohols (e.g., methanol, ethanol, etc.), esters (e.g., ethyl acetate), and ketones (e.g., acetone) when the compound is oleophilic or as an aqueous solution when the compound is hydrophilic. In adding the compound as an aqueous solution thereof, it is sometimes convenient for dissolution to use an alkaline aqueous solution thereof.

In adding the compound of the general formula (II) or (III) to a silver halide photographic material, the compound may be added at any period of from the start of the chemical ripening to the coating but it is preferred to add the compound after the end of the chemical ripening of the silver halide emulsion. Furthermore, it is particularly preferred to add the compound to the coating composition of a silver halide photographic emulsion prepared for coating.

The silver halide photographic emulsions used in this invention can be prepared using the methods as described in, for example, P. Glafkides; *Chimie et Physique Photographique;* Paul Montel (1967); G. F. Duffin; *Photographic Emulsion Chemistry;* The Focal Press (1966); and V. L. Zelikman et al; *Making and Coating Photographic Emulsions;* The Focal Press (1964). That is, an acid method, a neutral method, an ammonia method, etc., may be used desirably for the purpose and also a single jet method, a double jet method, and a combination of such methods may be used as the method of reacting a soluble silver salt and a soluble halide.

The so-called reverse mixing method, that is, a method in which silver halide grains are formed in the presence of an excessive amount of silver ions can be used. One mode of the simultaneous mixing method, the so-called controlled double jet method, that is, the method in which the value of the pAg of the liquid phase in which the silver halide grains are formed is maintained at constant value, can be used. According to this method, silver halide emulsions having a regular crystal form and an almost uniform grain size are obtained.

The silver halide grains in the silver halide emulsions may have a regular crystal form such as a cubic crystal form and an octahedral crystal form, or may be grains having an irregular crystal form such as a spherical crystal form and a plate crystal form, or further may be grains having a composite crystal form composed of these crystal forms.

The interior and the surface layer of the silver halide grains may be different or the silver halide grains may be a uniform phase throughout the grains.

During the formation or physical ripening process of the silver halide grains used in this invention, cadmium salts, zinc salts, lead salts, thallium salts, the salts or complex salts of rhodium and other elements belonging to Group VIII of the periodic table, or iron salts or iron complex salts may be present with the silver halide grains.

Moreover, two or more kinds of silver halide emulsions separately prepared may be used as a mixture thereof.

After the formation of the silver halide grains or after the physical ripening of the silver halide grains, soluble salts are usually removed therefrom and for the purpose, the well-known noodle water-washing method, in which soluble salts are removed from the silver halide emulsion by gelling the gelatin and washing it with water may be used or further a flocculation method in which inorganic salts composed of a multivalent anion (e.g., sodium sulfate), anionic surface active agents, anionic polymers (e.e., polystryenesulfonic acid), or gelatin derivatives (e.g., aliphatic acylated gelatin, aromatic acylated gelatin, aromatic carbamoylated gelatin, etc.,) are utilized may be employed. Also, the step of removing the soluble salts may be omitted.

As the silver halide emulsion, a primitive silver halide emulsion, that is, a silver halide emulsion which has not been chemically sensitized can be used but a chemically sensitized silver halide emulsion is usually employed in this invention. For chemical sensitization, it is preferred to employ a sulfur sensitization method using a sulfur-containing compound which can react with silver ion or active gelatin. However, a noble metal sensitization method using a compound of a noble metal (e.g., gold) may be used in combination with the sulfur sensitization method. For this noble metal sensitization, the complex salts of the metals belonging to Group VIII of the periodic table, such as gold, platinum, iridium, palladium, etc., can be used and specific examples thereof are described in U.S. Pat. No. 2,448,060 and British Pat. No. 618,061.

The photographic material of this invention may contain an antifoggant in the silver halide emulsion layer or in another hydrophilic colloid layer. Examples of suitable antifoggants are 1,2,3-triazole compounds (in particular, benzotriazoles), benzothiazolium compounds and benzimidazoles.

Moreover, if a small amount of an iodide compound such as, for example, potassium iodide, is added to the silver halide photographic emulsion after the formation of the silver halide grains, before the chemical ripening of the silver halide emulsion, after the chemical ripening, or before coating, the effect of this invention is enhanced further. A suitable amount of the iodide added is about $10^{-4}$ to about $10^{-2}$ mole/mole-Ag.

The photographic silver halide emulsions used in this invention may be spectrally sensitized using methine dyes and other dyes. Examples of suitable dyes which can be used for sensitization include cyanine dyes, merocyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. These dyes can contain nuclei usually present in cyanine dyes as basic heterocyclic nuclei. That is, these dyes may contain pyrroline nuclei, oxazoline nuclei, thiazoline nuclei, pyrole nuclei, oxazole nuclei, thiazole nuclei, selenazole nuclei, imidazole nuclei, tetrazole nuclei, pyridine nuclei, nuclei formed by fusing an aliphatic hydrocarbon ring to these nuclei and nuclei formed by fusing an aromatic hydrocarbon ring to these nuclei, such as indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei, etc. The carbon atoms of these nuclei may be substituted.

The merocyanine dyes or complex merocyanine dyes can contain 5-membered or 6-membered heterocyclic nuclei such as pyrazolin-5-one nuclei, thiohydantoin nuclei, 2-thiooxazolidin-2,4-dione nuclei, thiazolidin-2,4-dione nuclei, rhodanine nuclei, thiobarbituric acid nuclei, etc., as nuclei having a ketomethylene structure.

Examples of useful sensitizing dyes are described in, for example, German Pat. No. 929,080; U.S. Pat. Nos. 2,231,658; 2,493,748; 2,503,776; 2,519,001; 2,912,329; 3,656,959; 3,672,897; 3,694,217; British Pat. No. 1,242,588 and Japanese Patent Publication No. 14,030/'69.

These sensitizing dyes may be used individually or as a combination thereof and a combination of sensitizing dyes is frequently used for the purpose of supersensitization. Specific examples of suitable sensitizing dyes are described in, for example, U.S. Pat. Nos. 2,688,545; 2,977,229; 3,397,060; 3,522,052; 3,527,641; 3,617,293; 3,628,964; 3,666,480; 3,679,428; 3,703,377; 3,769,301; 3,814,609; and 3,837,862; British Patent No. 1,344,281; and Japanese Patent Publication No. 4936/'68.

A dye which does not provide spectral sensitization by itself or a material which does not substantially absorb visible light but exhibits a supersensitizing effect may be incorporated in the silver halide emulsion together with the sensitizing dye. For example, the silver halide emulsion may contain an aminostilbene compound substituted with a nitrogen-containing heterocyclic group (e.g., the compounds as described in U.S. Pat. Nos. 3,635,721 and 2,933,390), an aromatic organic acid formaldehyde condensation product (e.g., U.S. Pat. No. 3,743,510), etc. Also, the combinations described in U.S. Pat. Nos. 3,615,613; 3,615,641; 3,617,295 and 3,635,721.

The photographic materials of this invention may further contain water-soluble dyes in various layers for various purposes to prevent light scattering, for antihalation, etc. Suitable examples of these dyes are oxonole dyes, hemioxonole dyes, styryl dyes, merocyanine dyes, cyanine dyes, and azo dyes. Specific examples of the dyes which can be used in this invention for these purposes are described in, for example, British Pat. No. 584,609 and 1,177,429; Japanese Patent Application (OPI) Nos. 85,130/'73; 99,520/'74 and 114,420/'74; and U.S. Pat. Nos. 2,274,782; 2,533,472; 2,956,876; 3,148,187; 3,177,078; 3,247,127; 3,540,887; 3,575,704; 3,653,905 and 3,718,472.

The photographic material of this invention may contain an inorganic or organic hardening agent in a suitable hydrophilic colloid layer. For example, chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloyl-hexahydro-s-triazine, bis(vinylsulfonyl)methyl ether, etc.), active halogen compounds (e.g., 2,4-dichloro-6-hydroxy-s-triazine, etc.), mucohalic acids (e.g., mucochloric acid, mucophenoxychloric acid, etc.), isooxazoles, dialdehyde starch, 2-chloro-6-hydroxytriazinylated gelatin, and the like may be used individually or as combination thereof. Specific examples of these compounds are described in, for example, U.S. Pat. Nos. 1,870,354; 2,080,019; 2,726,162; 2,870,013; 2,983,611; 2,992,109; 3,047,394; 3,057,723; 3,103,437; 3,321,313; 3,325,287; 3,362,827; 3,539,644; 3,543,292; British Patent Nos. 676,628; 825,544 and 1,270,578; German Patent Nos. 872,153 and 1,090,427 and Japanese Patent Publication Nos. 7133/'59 and 1872/'71.

The photographic materials of this invention may further contain various surface active agents for various purposes such as as coating agents, antistatic agents, slip improving agents, emulsification dispersing agents, and adhesion preventing agents as well as for improving photographic properties (for example, development acceleration, contrast increase, and sensitization).

For example, nonionic surface active agents such as saponin (steroids), alkylene oxide derivatives (such as polyethylene glycol, polyethylene glycol/polypropylene glycol condensates, polyethylene glycol alkyl or alkylaryl ethers, polyethylene glycol esters, polyethylene glycol sorbitan esters, polyalkylene glycol alkylamines or amides or siliconepolyethylene oxide adducts), glycidol derivatives (such as alkenylsuccinic acid polyglycerides or alkylphenol polyglycerides), aliphatic esters of polyvalent alcohols, alkyl esters of sucrose, urethanes or ethers; anionic surface active agents containing an acidic group such as a carboxy group, a sulfo group, a phospho group, a sulfuric ester group or a phosphoric ester group, such as triterpenoid type saponin, alkylcarboxylates (salts), alkylsulfonates (salts), alkylbenzenesulfonates (salts), alkylnaphthalenesulfonates (salts), alkylsulfates, alkylphosphates, N-acyl-N-alkyltaurines, sulfosuccinates, sulfoalkylpolyoxyethylene alkylphenyl ethers or polyoxyethylene alkylphosphates; amphoteric surface active agents such as amino acids, aminoalkylsulfonic acids, aminoalkylsulfuric esters, aminoalkylphosphoric esters, alkylbetaines, amineimides or amine oxides; and cationic surface active agents such as alkylamine salts, aliphatic or aromatic quaternary ammonium salts, (such as pyridinium or imidazolium salts) or phosphonium or sulfonium salts containing an aliphatic or heterocyclic ring can be used.

Specific examples of these surface active agents are those described in, e.g., U.S. Pat. Nos. 2,240,472, 2,831,766, 3,158,484, 3,210,191, 3,294,540 and 3,507,660, British Pat. Nos. 1,012,495, 1,022,878, 1,179,290 and 1,198,450, Japanese Patent Application (OPI) No. 117,414/75, U.S. Pat. Nos. 2,739,891, 2,823,123, 3,068,101, 3,415,649, 3,666,478 and 3,756,828, British Pat. No. 1,397,218, U.S. Pat. Nos. 3,133,816, 3,441,413, 3,475,174, 3,545,974, 3,726,683 and 3,843,368, Belgian Pat. No. 731,126, British Pat. Nos. 1,138,514, 1,159,825 and 1,374,780, Japanese Patent Publications 378/65, 379/65 and 13,822/68, U.S. Pat. Nos. 2,271,623, 2,288,226, 2,944,900, 3,253,919, 3,671,247, 3,772,021, 3,589,906 and 3,754,924, German Patent Application (OLS) No. 1,961,638, Japanese Patent Application (OPI) No. 59,025/75, etc.

The silver halide photographic emulsions used in this invention may further contain dispersions of water-insoluble or water sparingly soluble synthetic polymers for improving the dimensional stability of the photographic materials. Examples of suitable synthetic polymers are polymers or copolymers of alkyl (metha)acrylates, alkoxyalkyl (metha)acrylates, glycidyl (metha)acrylates, (metha)acrylamides, vinyl esters (for example, vinyl acetate), acrylonitrile, olefins, styrene or combinations thereof, or combinations of the above-illustrated monomers and acrylic acid, methacrylic acid, $\alpha,\beta$-unsaturated dicarboxylic acids, hydroxyalkyl (metha)acrylates, sulfoalkyl (metha)acrylates, styrenesulfonic acid, etc.

Specific examples of these polymers which can be used in this invention are described in U.S. Pat. Nos. 2,376,005; 2,739,137; 2,853,457; 3,062,674; 3,411,911; 3,488,708; 3,525,620; 3,607,290; 3,635,715; and 3,645,740; British Pat. Nos. 1,186,699 and 1,307,373. The high contrast silver halide emulsions used in this invention are suitable for the reproduction of line images and since the dimensional stability is important for such purposes, it is preferred for the silver halide emulsions to contain such polymer dispersions.

In the case of color photographic light-sensitive materials, all ketomethylene yellow dye-forming couplers can advantageously be used. Typical examples thereof are couplers of the benzoylacetanilide series, pivalylacetanilide series, etc. Further, all magenta dye-forming couplers of the pyrazolone series, indazolone series, etc., can advantageously be used. In addition, all cyan dye-forming couplers of the phenol series, naphthol series, etc., can advantageously be used. These couplers may contain a coupling-off group at the active carbon atom positioned at the coupling site. Those couplers rendered nondiffusible with a ballast group are preferred. A large number of ballasted compounds are well known for these couplers.

These dye-forming couplers can be dispersed in a hydrophilic colloid in any known manner. They can advantageously be dispersed with the use of a coupler solvent as described in U.S. Pat. No. 2,322,027, etc.

The photographic materials of this invention may be exposed in a conventional manner. That is, various light sources such as natural light (sun light), a tungsten lamp, a fluorescent lamp, a mercury lamp, a xenon arc lamp, a xenon flash lamp, a cathode ray flying spot, etc., can be employed. The exposure time may, as a matter of course, range from 1/1000 sec. to 1 sec., which is usually employed for incamera exposure but may be $1/10^4$ to $1/10^6$ sec. in the case of using, for example, a xenon flash lamp, or may be longer than 1 sec.

If desired, the spectral composition of the light used for the exposure can be controlled using color filters. Also, the fluorescence emitted by the excitation by ionization radiation or a laser beam can be used for the exposure. Also, electron beams, X-rays, gamma rays, $\alpha$-rays, etc., may be also used for the exposure.

The photographic materials of this invention can be processed using known methods. In this case, known processing solutions can be used. The processing temperature is usually from about 18° C. to about 50° C. but may be lower than about 18° C. or higher than about 50° C. if necessary.

This invention is useful for image formation by a development process (black and white photographic process) for forming silver images. Further, the invention can also be applied to a color photographic process using a development process in which dye images are formed.

The developer used for black-and-white photographic processing contains, as a developing agent, a combination of 3-pyrazolidone compounds (such as 1-phenyl-3-pyrazolidone) with hydroquinone compounds (such as hydroquinone), in which the 3-pyrazolidone compound is preferably used in an amount of 0.01 g/l to 8 g/l, most preferably 0.05 g/l to 5 g/l of the developer and the hydroquinone compound is preferably used in an amount of 2 g/l to 80 g/l most preferably 5 g/l to 60 g/l of the developer. Moreover, the developers usually contain a known antioxidant, an alkali agent, a pH buffer or the like and, if desired, a dissolving aid, a color toning agent, a development accelerator, a surface active agent, an anti-foaming agent, a water softener, a hardener, a tackifier, etc., may be present. An anti-fogging agent (such as an alkali metal halide or benzotriazole) may be present in the developer.

Color developers commonly used in the art can also be used in the present invention, i.e., any alkaline aqueous solution containing a color-developing agent. All known dye-forming aromatic primary amine developers such as phenylenediamines (e.g., N,N-diethyl-p-phenylenediamine, N-ethyl-N-hydroxyethyl-p-phenylenediamine, N-ethyl-N-hydroxyethyl-2-methyl-p-phenylenediamine, N-ethyl-$\beta$-N-methanesulfonamidoethyl-3-methyl-4-aminoaniline, N,N-diethyl-2-methyl-p-phenylenediamine, and the sulfonates, hydrochlorides and sulfites thereof, etc.) can be used as the color-developing agents. The color developer may further contain generally used additives such as a sulfite, carbonate, bisulfite, alkali metal bromides or iodides, benzyl alcohol and the like.

Black and white development is more preferred for the present invention.

According to this invention, even when development is carried out using a developer containing more than about 0.1 mol/l of sulfite ions, a $\gamma$ of more than 8 can be obtained. The pH of the developer is preferably about 11 to about 12.3. When the pH is low, it is difficult to obtain the sensitizing effect and the high contrast effect of the present invention. If the pH exceeds about 12.3, the developer is unstable even when a high concentration of sulfite ions is present, and it is difficult to maintain stable photographic characteristics for more than 3 days under usual use conditions.

Those fixing solutions having a composition generally employed in the art can be used in the present invention. Not only thiosulfates and thiocyanates but also organic sulfur compounds known as fixing agents can be used as fixing agents in the present invention.

Suitable preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thia-1,5-pentanediol, 3,6-dithia-1,8-octanediol, 9-oxo-3,6,12,15-tetrathia-1,17-heptadecanediol, etc., water-soluble sulfur containing organic dibasic acids and water-soluble salts thereof such as ethylenebisthioglycollic acid and the sodium salt thereof, etc., imidazolidinethiones such as methylimidazolidinethione, etc. Further, the fixing agents described in L. F. A. Mason, *Photographic Processing Chemistry*, pages 187 to 188, Focal Press (1966) are also preferred.

Other processing solutions, e.g., a bleaching solution, a fixing solution, a stabilizing solution, etc., known in the art also may advantageously be used. These processing solutions may be used in combination, e.g., as a bleach-fixing solution, a fix-stabilizing solution or a bleach-fix-stabilizing solution.

Such solutions are well known in the art, and any of such known solutions are useful. A bleaching solution contains a silver oxidizing agent(s), e.g., water-soluble ferricyanides, a simple water-soluble ferric, cupric or cobaltic salt, and complex salts or an alkali metal and polyvalent cations with an organic acid. Typical examples of polyvalent cations are ferric ions, cobaltic ions, cupric ions, etc. Typical examples of the organic acids are ethylenediaminetetraacetic acid, nitrilotriacetic acid, etc.

The invention is more specifically explained below by reference to the following examples. Unless otherwise indicated herein all parts, percents, ratios and the like are by weight.

EXAMPLE 1

A silver bromide emulsion having a mean grain size of 0.25 micron was prepared by adding simultaneously an aqueous silver nitrate solution and an aqueous potassium bromide solution to an aqueous gelatin solution maintained at 50° C. over a period of 50 minutes while maintaining the pAg of the system at 7.9 during the addition. After removing soluble salts from the emulsion formed, sodium thiosulfate was added to the solution in an amount of 43 mg per mole of silver bromide and the emulsion was chemically ripened for 60 minutes at 60° C. The silver halide emulsion thus prepared contained 120 g of gelatin per mole of silver bromide. The internal sensitivity of the silver halide emulsion could be substantially ignored as compared with the surface sensitivity thereof.

To the silver bromide emulsion prepared were added Compound (I-2) and one of Compounds (II-1), (II-2), (II-7), (II-9) and (III-1) as shown in Table 1 below according to this invention and after further adding thereto 2-hydroxy-4,6-dichloro-1,3,5-triazine sodium salt as a hardening agent, the resultant mixture was coated on a cellulose triacetate film at a coverage of 45 mg/100 cm² of silver.

Each of the samples thus prepared was exposed for 1 sec. through an optical wedge, developed for 5 minutes at 20° C. using the developer having the following composition

| | |
|---|---|
| 1-phenyl-3-pyrazolidone | 0.2 g |
| Hydroquinone | 25.0 g |
| Potassium Carbonate | 15.0 g |
| Sodium Sulfite (anhydrous) | 72.0 g |
| Potassium Hydroxide | 23.0 g |
| Potassium Bromide | 3.0 g |
| Tetrasodium Ethylenediamintetraacetic acid | 2.0 g |
| 5-methyl benzotriazole | 0.25 g |
| Water to make | 1 l |
| | (pH ≈ 11.7) | and then processed in accordance with the following procedures:

| | |
|---|---|
| Stopping | 20° C. 30 seconds |
| Fixing | 20° C. 5 minutes |
| Washing | |
| Drying | |

The stopping bath and the fixing bath had the following composition.

| | |
|---|---|
| Stopping Bath | |
| Acetic Acid (28% aq. soln.) | 48 ml |
| Water to make | 1 liter |
| Fixing Bath | |
| Sodium Thiosulfate | 240 g |
| Sodium Sulfite (anhydrous) | 15 g |
| Acetic Acid (28% aq. soln.) | 48 ml |
| Boric Acid | 7.5 g |
| Potassium Alum | 15 g |
| Water to make | 1 liter |

The photographic properties obtained are shown in Table 1 below. In the table, the relative sensitivity is the relative value of the reciprocal of the exposure amount providing an optical density 2.0 above fog.

TABLE 1

| Run No. | Compound (I) Compound | Compound (I) Amount (mole/mole Ag) | Compound (II) Compound | Compound (II) Amount (mole/mole Ag) | Specific Sensitivity | Gamma | Fog |
|---|---|---|---|---|---|---|---|
| 1 | — | — | — | — | 100 | 5 | 0.06 |
| 2 | (I-2) | $2.1 \times 10^{-2}$ | — | — | 250 | 16 | 0.06 |
| 3 | — | — | (II-1) | $9.4 \times 10^{-3}$ | 220 | 5 | 0.06 |
| 4 | (I-2) | $2.1 \times 10^{-2}$ | (II-1) | $9.4 \times 10^{-3}$ | 705 | 16 | 0.06 |
| 5 | — | — | (II-2) | $6.3 \times 10^{-3}$ | 160 | 5 | 0.06 |
| 6 | (I-2) | $2.1 \times 10^{-2}$ | (II-2) | $6.3 \times 10^{-3}$ | 840 | 16 | 0.06 |
| 7 | — | — | (II-7) | $5.2 \times 10^{-3}$ | 250 | 5 | 0.06 |
| 8 | (I-2) | $2.1 \times 10^{-2}$ | (II-7) | $5.2 \times 10^{-3}$ | 855 | 16 | 0.06 |
| 9 | — | — | (II-9) | $4.8 \times 10^{-3}$ | 275 | 5 | 0.06 |
| 10 | (I-2) | $2.1 \times 10^{-2}$ | (II-9) | $4.8 \times 10^{-3}$ | 1300 | 16 | 0.06 |
| 11 | — | — | (III-1) | $5.7 \times 10^{-3}$ | 160 | 5 | 0.06 |
| 12 | (I-2) | $2.1 \times 10^{-2}$ | (III-1) | $5.7 \times 10^{-3}$ | 910 | 18 | 0.06 |

In Table 1, Run No. 4, 6, 8, 10 and 12 are of this invention while Run No. 1, 2, 3, 5, 7, 9 and 11 are for comparison.

As is clear from the results shown in Table 1 above, the use of Compound (I-2) alone or Compound (II-1), (II-2), (II-7), (II-9) or (III-1) alone results in a sensitization effect of from 1.6 times to 2.8 times but when the compound of general formula (I) is used together with the compound of general formula (II) or (III), an unexpectedly high sensitization effect is obtained. Furthermore, in the latter case, the gamma value was very high and the increase of fog was very low.

EXAMPLE 2

Photosensitive film samples were prepared using the same procedure as described in Example 1 except that Compound (I-1), (I-4) or (I-7) was used in place of Compound (I-2) in the sample of Run No. 4 as shown in Table 2 below and $9.4 \times 10^{-3}$ mole/mole-Ag of Compound (II-1) was used. Furthermore, samples which did not contain any Compound (II-1) were also prepared in the same manner as above.

Each of the samples was exposed for 1 sec. through an optical wedge, developed for 3 minutes at 20° C. in the same developer as described in Example I except that 5-methylbenzotriazole was used in an amount of 0.35 g and pH of the developer was adjusted to 12.1 by adding potassium hydroxide, and then processed in accordance with the procedures described in Example 1.

The photographic properties obtained are shown in Table 2 below.

TABLE 2

| Run No. | Compound (I) Compound | Amount (mole/mole Ag) | Compound (II-1) Amount (mole/mole Ag) | Specific Sensitivity | Gamma | Fog |
|---|---|---|---|---|---|---|
| 101 | — | — | — | 100 | 5 | 0.06 |
| 102 | — | — | $9.4 \times 10^{-3}$ | 230 | 5 | 0.06 |
| 103 | (I-1) | $2.1 \times 10^{-2}$ | — | 350 | >20 | 0.06 |
| 104 | " | " | $9.4 \times 10^{-3}$ | 985 | >20 | 0.06 |
| 105 | (I-4) | $1.7 \times 10^{-2}$ | — | 275 | 19 | 0.06 |
| 106 | " | " | $9.4 \times 10^{-3}$ | 790 | 19 | 0.06 |
| 107 | (I-7) | $1.0 \times 10^{-2}$ | — | 275 | 13 | 0.06 |
| 108 | " | " | $9.4 \times 10^{-3}$ | 780 | 13 | 0.06 |

As is clear from the results shown in Table 2 above, the use of Compound (II-1) alone provides a sensitization of about 2 times but the sensitization effect is 7.5 to 10 times when Compound (I-1), (I-4) or (I-7) is further added. On considering that the sensitization effect due to Compound (I-1), (I-4) or (I-7) alone is 2.6 to 3.5 times, the sensitivity obtained by using a compound of general formula (I) and the compound of general formula (II) together clearly is unexpected over the effects obtained with use of each compound individually.

EXAMPLE 3

To the silver bromide emulsion described in Example 1 were added Compound (I-2) and Compound (II-1) as shown in Table 3 and after further adding thereto following additives:

| Coupler (mazenta) | 1-(2,4,6-trichlorophenyl)-3-{(2-chloro-5-tetradecanamido)anilino}-5-pyrazolone |
| Spectral Sensitizer | Bis-[2-{1-ethyl-3-(3-sulfopropyl)-5,6-dichlorobenzimidazole}]trimethynecyanine sodium salt |
| Hardener | Bisvinylsulfonehydroxypropane |
| Coating additive | Sodium-p-dodecylbenzenesulfonic acid and sodium-p-nonylphenoxypoli(ethyleneoxy) propan sulfonic acid |
| Antifoggant | 5-methylbenzotriazole |

The resultant mixture was coated on a cellulose triacetate film at coverage of 45 mg/100 cm² of silver.

Each of samples thus prepared was exposed for 1/20 sec. through a yellow filter and an optical wedge and then processed in accordance with the folllowing procedures:

| 1. color development | 3 minutes 15 seconds (38° C.) |
| 2. bleaching | 6 minutes 30 seconds |
| 3. washing | 3 minutes 15 seconds |
| 4. fixing | 6 minutes 30 seconds |
| 5. washing | 3 minutes 15 seconds |
| 6. stabilizing | 3 minutes 15 seconds |

The color developer, the belaching solution, the fixing solution and the stabilization solution had the following composition.

| Color Developer | |
|---|---|
| Sodium Nitrirotriacetic acid | 1.0 g |
| Sodium Sulfite | 4.0 g |
| Sodium Carbonate | 30.0 g |
| Potassium Bromide | 1.4 g |
| Hydroxylamine sulfate | 2.4 g |
| N-ethyl-N-hydroxyethyl-p-phenylenediamine sulfate | 4.5 g |
| Sodium Hydroxide to adjust pH at 11.8 | |
| Water to make | 1 l |
| Bleaching Solution | |
| Ammonium Bromide | 160.0 g |
| Aqueous Ammonium (28%) | 25.0 ml |
| Ethylenediaminetetraacetic acid sodium iron salt | 130 g |
| Glacial acetic acid | 14 ml |
| Water to make | 1 l |
| Fixing Solution | |
| Sodium tetratriphosphate | 2.0 g |
| Sodium Sulfite | 4.0 g |
| Ammonium trisulfate (70%) | 175.0 ml |
| Sodium hydrogensulfite | 4.6 g |
| Water to make | 1 l |
| Stabilization Solution | |
| Formaline | 8.0 ml |
| Water to make | 1 l |

Then, density of the samples thus processed was measured and the results are shown in the following Table 3.

TABLE 3

| Run No. | Compound (I) Compound | Amount (mole/mole Ag) | Compound (II) Compound | Amount (mole/mole Ag) | Specific Sensitivity | Gamma | Fog |
|---|---|---|---|---|---|---|---|
| 301 | — | — | — | — | 100 | 5.5 | 0.04 |
| 302 | — | — | (II-1) | $8.2 \times 10^{-2}$ | 180 | 5.5 | 0.04 |
| 303 | (I-2) | $2.3 \times 10^{-2}$ | — | — | 225 | 16 | 0.04 |
| 304 | (I-2) | $2.3 \times 10^{-2}$ | (II-1) | $8.2 \times 10^{-2}$ | 550 | 16 | 0.04 |

The increase of sensitivity and Gamma value using Compound (I) together with Compound (II) was shown when a color developer was used.

While the invention has been described in detail and with reference to specific embodiments thereof, it will be apparent to one skilled in the art that various changes and modifications can be made therein without departing from the spirit and scope thereof.

What is claimed is:

1. A negative image forming process which comprises imagewise exposing to light a photographic light-sensitive material comprising a support having thereon at least one silver halide photographic emulsion layer containing substantially surface latent image type monodispersed silver halide grains and providing a negative image, at least one hydrophilic colloid layer of said photographic material containing a compound represented by the general formula (I)

$$R^1NHNHCOR^2 \qquad (I)$$

in an amount of about $10^{-4}$ to about $10^{-1}$ mole/mole-Ag, wherein $R^1$ represents an aryl group and $R^2$ represents a hydrogen atom, a phenyl group, or an unsubstituted alkyl group having 1 to 3 carbon atoms; and a compound represented by the general formula (II) or (III);

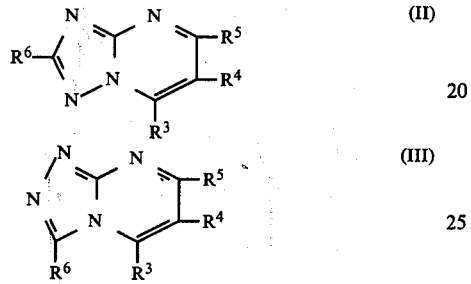

wherein $R^3$, $R^4$, $R^5$ and $R^6$, which may be the same or different, each represents a hydrogen atom, an alkyl group, an aryl group, an amino group, a hydroxyl group, an alkoxy group, an alkylthio group, a carbamoyl group, a halogen atom, a cyano group, a carboxyl group, an alkoxycarbonyl group, or a heterocyclic ring; wherein said $R^3$ and $R^4$ or said $R^4$ and $R^5$ may combine and form a 5-membered or 6-membered ring and wherein at least one of $R^3$ and $R^5$ represents a hydroxyl group and developing said photographic light-sensitive material with a developing solution containing a developing agent selected from the group consisting of a phenylenediamine compound and a combination of a 3-pyrazolidone compound with a hydroquinone compound and, containing about 0.1 mole/liter or more of sulfite ion and having a pH of about 11.0 to about 12.3.

2. The negative image forming process of claim 1, wherein said hydrophilic colloid layer is said silver halide photographic emulsion layer containing substantially surface latent image type monodispersed silver halide grains.

3. The negative image forming process of claim 1, wherein $R^1$ is a monocyclic or bicyclic aryl group, which may be substituted with one or more substituents which are not electron attracting.

4. The negative image forming process of claim 1, wherein $R^1$ is a monocyclic or bicyclic aryl group which may be substituted with one or more of an alkyl group having 1 to 20 carbon atoms which may be straight chain or branched chain, an aralkyl group in which the alkyl moiety has 1 to 3 carbon atoms and may be straight chain or branched chain, an alkoxy group having 1 to 20 carbon atoms in which the alkyl moiety may be straight chain or branched chain, an amino group mono- or di-substituted with an alkyl group having 1 to 20 carbon atoms and which may be straight chain or branched chain, an aliphatic acylamino group having 2 to 21 carbon atoms and which may be staight chain or branched chain and an aromatic acylamino group which contains a monocyclic aryl moiety;

$R^2$ is a hydrogen atom, a phenyl group which may be substituted with one or more of a halogen atom, a cyano group, a trifluoromethyl group, a carboxy group and a sulfo group;

$R^3$, $R^4$, $R^5$ and $R^6$ each represents a hydrogen atom; an alkyl group which may be straight chain, branched chain or cyclic and which may be substituted with one or more of a monocyclic or bicyclic aryl group, a heterocyclic group comprising a 5- of 6-membered ring which may contain one or more of a nitrogen atom, an oxygen atom and a sulfur atom as hetero atoms, a halogen atom, a carboxyl group, an alkoxycarbonyl group, an alkoxy group in which the alkyl moiety may be straight chain or branched chain and a hydroxyl group; a monocyclic aryl group which may be substituted with one or more of an alkyl group which may be straight chain, branch chain or cyclic, a halogen atom, a carboxyl group, an alkoxycarbonyl group in which the alkyl moiety may be straight chain or branched chain, a hydroxyl group and an alkoxy group in which the alkyl moiety may be straight chain or branched chain; an amino group which may be mono- or di-substituted with one or more of an alkyl group which may be straight chain, branched chain or cyclic and an acyl group in which the alkyl moiety may be straight chain or branched chain; a hydroxyl group; an alkoxy group in which the alkyl moiety may be straight chain or branched chain; an alkylthio group in which the alkyl moiety may be straight chain or branched chain; a carbamoyl group which may be mono- or di-substituted with one or more of an alkyl group which may be straight chain, branched chain or cyclic and a monocyclic or bicyclic aryl group; a halogen atom; a cyano group; a carboxyl group; an alkoxycarbonyl group in which the alkyl moiety may be straight chain or branched chain; or a heterocyclic group comprising a 5- or 6-membered ring which may contain one or more of a nitrogen atom, an oxygen atom and a sulfur atom as heteroatoms.

5. The negative image forming process of claim 1, wherein $R^6$ has the general formula (IV)

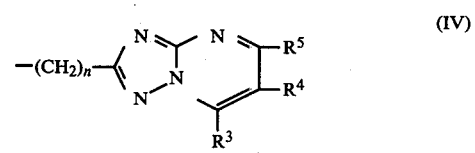

wherein $R^3$, $R^4$ and $R^5$ each has the same meaning as in the general formula (II) or (III) and n represents 2 or 4.

6. The negative image forming process of claim 1, wherein the compound of general formula (I) is a compound represented by general formula (Ia)

$$R^1NHNHCHO \qquad (Ia)$$

wherein $R^1$ has the same meaning as in the general formula (I).

7. The negative image forming process of claim 6, wherein the compound of the general formula (Ia) is a compound reperesented by general formula (Ib)

$$R^{11}NHNHCHO \qquad (Ib)$$

wherein $R^{11}$ represents an unsubstituted phenyl group or a tolyl group.

8. The image forming process of claim 1, wherein said developing solution contains a combination of a 3-pyrazolidone compound with a hydroquinone compound as a developing agent.

9. The image forming process of claim 8, wherein said 3-pyrazolidone compound is 1-phenyl-3-pyrazolidone and said hydroquinone compound is hydroquinone.

10. The image forming process of claim 1, wherein said developing solution further contains a color coupler and said developing agent is a phenylenediamine compound.

* * * * *